United States Patent [19]

Brinkmeyer et al.

[11] Patent Number: 5,243,122

[45] Date of Patent: Sep. 7, 1993

[54] DEHYDROGENATION PROCESS CONTROL

[75] Inventor: Francis M. Brinkmeyer; Kelly B. Savage; Steven D. Bridges, all of Bartlesville, Okla.

[73] Assignee: Phillips Petroleum Company, Bartlesville, Okla.

[21] Appl. No.: 814,544

[22] Filed: Dec. 30, 1991

[51] Int. Cl.$^5$ ............................................. C07C 5/327
[52] U.S. Cl. .................................... 585/654; 585/660; 585/922; 585/950; 585/910; 208/DIG. 1
[58] Field of Search ............ 585/654, 660, 922, 950, 585/910; 208/DIG. 1

[56] References Cited

U.S. PATENT DOCUMENTS

| | | | |
|---|---|---|---|
| 3,607,091 | 9/1971 | Boyd | 208/143 |
| 4,132,529 | 1/1979 | Schwimmer | 585/401 |
| 4,132,530 | 1/1979 | Schwimmer | 585/263 |
| 4,229,609 | 10/1980 | Hutson, Jr. et al. | 585/660 |
| 4,234,410 | 11/1980 | Keeley | 364/500 |
| 4,290,110 | 9/1981 | Makovec | 364/500 |
| 4,879,424 | 11/1989 | Harandi | 585/322 |
| 4,891,464 | 1/1990 | Staggs | 585/440 |
| 4,902,849 | 2/1990 | McKay et al. | 585/660 |

Primary Examiner—Patrick P. Garvin
Assistant Examiner—E. D. Irzinski
Attorney, Agent, or Firm—George E. Bogatie

[57] ABSTRACT

In a steam active catalytic process employing a fixed catalyst bed for the dehydrogenation of alkanes to alkenes wherein reaction temperatures above about 500° C. (932° F.) must be maintained for commercially feasible conversions, the decline in catalyst activity during a production period is slowed by maintaining a substantially constant temperature for the reaction effluent while allowing the average temperature of the fixed catalyst bed to rise during a production period.

6 Claims, 2 Drawing Sheets

DEHYDROGENATION PROCESS CONTROL

This invention relates to production of alkenes. In one aspect, it relates to a process for dehydrogenation of light alkane hydrocarbons. In another more specific aspect, it relates to a method and an apparatus for process control as applied to a dehydrogenation process for light alkane hydrocarbons.

BACKGROUND OF THE INVENTION

Various catalytic dehydrogenation processes for hydrocarbons are known by which less saturation and more reactive compounds are produced. Temperature control in dehydrogenation reactions of this type is considered crucial since the reactions are highly endothermic reactions which require closely controlled and relatively high temperatures for favorable equilibria, as well as for adequate reaction velocities. Reaction temperature control in these processes has been generally accomplished by maintaining a desired average temperature of the catalyst bed.

Active dehydrogenation catalysts employed in fixed-bed, fired-tube reactors, are usually employed in commercial operations for producing isobutene from isobutane. For example, it is known to commercially dehydrogenate light aliphatic hydrocarbons, such as isobutane, in the presence of catalysts which comprise a Group II metal aluminate, a Group IVA metal oxide, and a Group VIII metal.

It is also known in the art that the activity of such dehydrogenation catalysts will decline to an ineffective level after a period of about 6 hours to about 20 hours of continuous use. The decline in dehydrogenation catalyst activity is believed to be due to the formation of coke and polymers on the catalyst. In order to maintain catalyst activity, it has therefore been necessary to periodically regenerate the catalyst. This is usually done by cutting off the feed to the spent catalyst, and then treating the spent catalyst with a free oxygen containing gas and steam. Therefore production of the reactor is suspended during the regeneration period.

A primary object of this invention is to increase production of isobutene from isobutane in a dehydrogenation reactor by slowing the decline of catalyst activity. It is a more specific object of this invention to slow the decline in catalyst activity during continuous use of the catalyst in a dehydrogenation reactor by applying a more effective temperature control scheme.

It is a further object of this invention to provide an improvement for a hydrocarbon dehydrogenation process which is safe, simple, effective, efficient and economical.

SUMMARY OF THE INVENTION

In accordance with the present invention, it has been discovered that the decline in activity of a dehydrogenation catalyst during continuous use of the catalyst in a steam active reforming process is retarded, and a corresponding increase in production of alkenes from alkanes is achieved in a hydrocarbon dehydrogenation reactor by maintaining the temperature of the reaction effluent constant, while allowing the average temperature of the catalyst bed to rise during a production period.

In a preferred embodiment, the dehydrogenation catalyst comprises (i) at least one aluminate spinel selected from Group of IIA (e.g. aluminate spinel of Be and/or Mg and/or Ca and/or Sr and/or Ba) and Group IIB metal aluminates (e.g. aluminate spinel of Cd and/or Zn), (ii) at least one metal selected from the group of nickel, ruthenium, rhodium, palladium, osminum, iridium and platinum, and (iii) at least one compound of a metal selected from the group of germanium, tin and lead. The preferred catalyst composition comprises platinum, tin oxide and zinc aluminate, and optionally includes a binder of calcium aluminate as described in U.S. Pat. No. 4,902,849 to McKay et al.

The effluent temperature of dehydrogenation reaction products is maintained substantially constant by a relatively simple reactor firing control scheme, where the fuel gas firing to the reactor is set by a process temperature controller responsive to the measured reaction effluent temperature.

Additional objects and advantages of the invention will be apparent from the following detailed description of the preferred embodiment of the invention, as illustrated by the drawings in which:

DETAILED DESCRIPTION OF THE PREFERRED EMBODIMENT

The present invention is applicable to any hydrocarbon dehydrogenation process employing a fixed catalyst bed in which catalyst activity declines with continued use of the catalyst. The invention is particularly suitable for use in the presence of steam when a steam active dehydrogenation catalyst comprises a support selected from the group consisting of alumina, silica, magnesia, zirconia, alumina-silicates, Group II aluminate spinels and mixtures thereof, and the catalytic amount of at least one Group VIII metal.

Any suitable paraffin containing 2-8 carbon atoms per molecule, such as n-butane, isobutane, isopentane or mixtures thereof can be used as the feed in a dehydrogenation process to which the temperature control scheme of the present invention can be applied.

Figure 1:
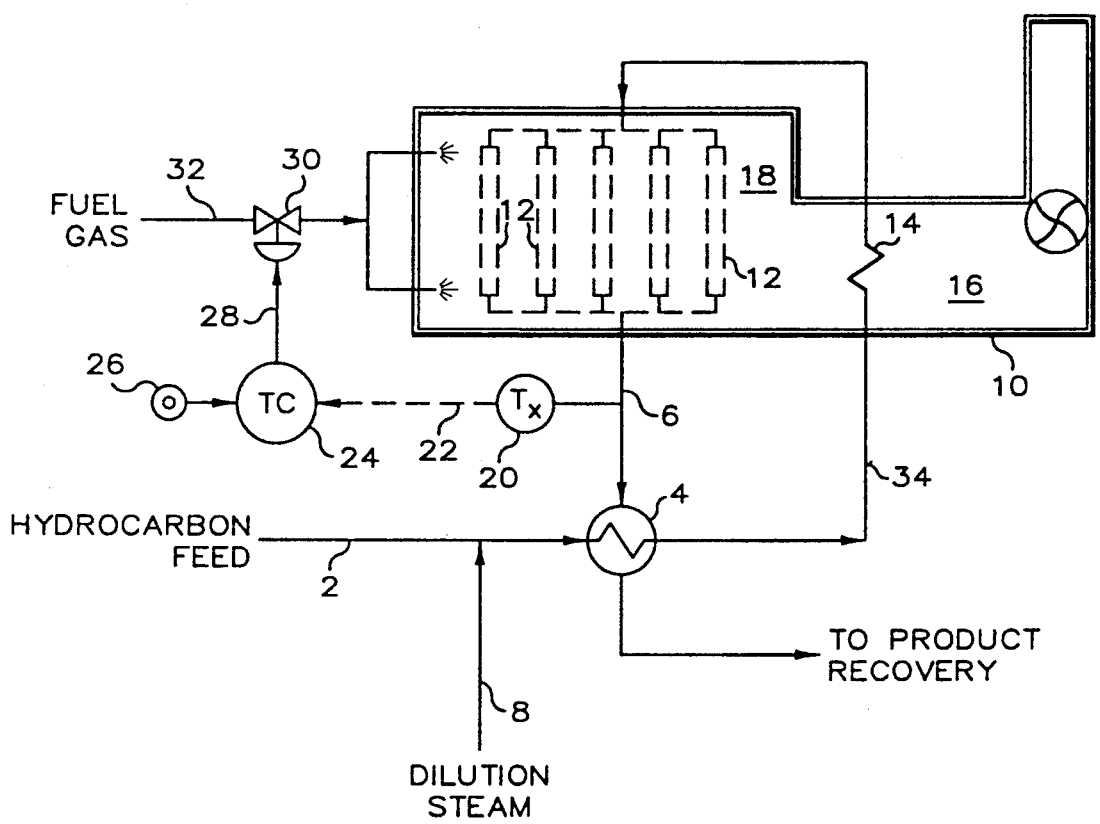
FIG. 1 is a simplified schematic diagram illustrating process flow of a dehydrogenation reaction and the associated control system of the present invention.

It will be appreciated by those skilled in the art that since FIG. 1 is schematic only, many items of equipment which would be needed in a commercial plant for successful operation have been omitted for the sake of clarity. Such items of equipment would include, for example, flow, pressure and additional temperature measuring instruments and corresponding process controllers, pumps, additional heat exchangers and valves, etc., and all these items would be provided in accordance with standard chemical engineering practice, and they play no part in the explanation of the present invention.

Referring now to FIG. 1, a liquid alkane feed, preferably isobutane, but which can be any dehydrogenatable hydrocarbon, is supplied via conduit 2 to a vaporizer 4 which may be supplied with a suitable heating medium such as steam, or as illustrated in FIG. 1, the liquid feed may be vaporized by heat exchange with reactor effluent flowing in conduit 6. Liquid isobutane flowing in conduit 2 is admixed with dilution steam flowing in conduit 8. The presence of steam diluent, which is added in a fixed ratio to hydrocarbon feed, reduces the partial pressure of the hydrocarbons, thus shifting equilibrium conditions for this system toward greater conversion. The dilution steam, which may be obtained from any suitable source, also tends to minimize coke buildup on the catalyst.

FIG. 1 illustrates a simplified dehydrogenation process employing a single fixed-bed, fired-tube reactor 10 with firing outside the catalyst filled tubes 12 to provide the heat of reaction. A single reactor 10, having a fixed catalyst bed arrangement which includes five catalyst filled tubes 12, is illustrated in FIG. 1. A large commercial plant, however, would generally employ a plurality of reactors, e.g., 8 parallel connected reactors with each reactor having hundreds of catalyst filled tubes of about four inches in diameter and about twelve feet in length, where 7 reactors will be dehydrogenating isobutane, while one reactor will be undergoing regeneration. In general, reaction cycle time is 7 hours on process and 1 hour on regeneration. However, in some situations, longer cycle times of 13/1 or more are possible. Although the instant invention is not intended to be so limited, a specific process cycle time of 26 hours is suggested as a possible optimum production cycle time.

The gaseous mixture of isobutane and steam flowing in conduit 34 is superheated in a furnace coil 14 in a convection section 16 of the fired reactor 10, and is then divided to flowing through a plurality of catalyst filled tubes 12 in the radiant section 18 of the fired reactor 10.

The product of the dehydrogenation process comprises primarily monoolefins (alkenes). By-products are CO, $CO_2$, diolefins and possibly aromatics. Cracked products including $C_1$, $C_2$ and $C_3$ hydrocarbons may also be present. When propane is used as feed material, primarily propylene is formed, when n-butane is used, primarily butene-1 and butene-2 are formed, when isobutane is used as feed material, primarily isobutene is formed and when isopentane is used, primarily isopentenes are formed. Fuel gas supplied to fired reactor 10 via conduit 32 and control valve 30 is set by process temperature controller 24.

The dehydrogenation and regeneration steps are conducted under any suitable conditions. Examples of dehydrogenation and regeneration conditions are disclosed, for example, in U.S. Pat. No. 4,229,609 to Hudson, Jr. et al., the disclosure of which concerning process conditions is incorporated herein by reference.

The dehydrogenation process described to this point in the detailed description of the invention is conventional. It is the temperature control applied to the dehydrogenation process that provides the novel feature of the present invention.

Although the invention is illustrated and described in terms of a specific reactor configuration, a specific heating scheme and a specific control system for the reactor, the invention is also applicable to different types and configurations or reactor heating schemes of reactors, e.g. where a $C_4$ raffinate stream is recycled and mixed with the feed flowing to the reactor, as well as different types of control system configurations which accomplish the purpose of the invention. Lines designated as signal lines in the drawings are electrical or pneumatic in this preferred embodiment. However, the invention is also applicable to mechanical, hydraulic or other signal means for transmitting information. In almost all control systems, some combination of these types of signals will be used. However, use of any other type of signal transmission, compatible with the process and equipment in use is within the scope of the invention.

The controllers shown may utilize the various modes of control such as proportional, proportional-integral, proportional-derivative, or proportional-integral-derivative. In this preferred embodiment, proportional-integral controllers are utilized but any controller capable of accepting two input signals and producing a scaled output signal, representative of a comparison of the two input signals, is within the scope of the invention. The operation of proportional-integral controllers is well known in the art. The output control signal of a proportional-integral controller may be represented as:

$$S = K_1 e + K_2 \int e \, dt$$

where
 S = output control signals;
 e = difference between two input signals; and
 $K_1$ and $K_2$ = constants.

The scaling of an output signal by a controller is well known in control system art. Essentially, the output of a controller may be scaled to represent any desired factor or variable. An example of this is where a desired temperature and an actual temperature are compared by a controller. The output could be a signal representative of a desired change in the flow rate of some fluid necessary to make the desired and actual temperture equal. On the other hand, the same output signal could be scaled to represent a percentage or could be scaled to represent a pressure change required to make the desired and actual temperature equal. If the controller output can range from 0 to 10 volts, which is typical, then the output signal could be scaled so that an output signal of 5 volts corresponds to 50 percent, some specified flow rate, or some specified pressure.

The various transducing means used to measure parameters which characterize the process and the various signals generated thereby may take a variety of forms or formats. For example, the control elements of the system can be implemented using electical analog, digital electronic, pneumatic, hydraulic, mechanical or other similar types of equipment or combinations of one or more of such equipment types. While the presently preferred embodiment of the invention preferably utilizes a combination of pneumatic control elements in conjunction with electrical analog signal handling and translation apparatus, the apparatus and method of the invention can be implemented using a variety of specific equipment available to and understood by those skilled in the process control art. Likewise, the format of the various signals can be modified substantially in order to accommodate signal format requirements of the particular installation, safety factors, the physical characteristics of the measuring or control instruments and other similar factors. For example, a raw flow measurement signal produced by a differential pressure orifice flow meter would ordinarily exhibit a generally proportional relationship to the square of the actual flow rate. Other measuring instruments might produce a signal which is proportional to the measured parameter, and still other transducing means may produce a signal which bears a more complicated, but known, relationship to the measured parameter. Regardless of the signal format or the exact relationship of the signal to the parameter or representation of a desired process value, it will bear a relationship to the measured parameter or desired value which permits designation of a specific measured or desired value by a specific signal value. A signal which is representative of a process measurement or desired process value is therefore one from which the information regarding the measured or desired value can be readily retrieved regardless of the exact mathematical relationship between the signal units and the measured or desired process units.

Referring again to FIG. 1, temperature transducer 20 in combination with a sensing device such as a thermocouple, which is operably located in conduit 6, establishes an output signal 22 which is representative of the actual temperature of reaction effluent flowing in conduit 6. Signal 22 is provided as a process variable input to temperature controller 24. Temperature controller 24 is also provided with a set point signal 26 which is an operator-entered signal representative of the desired effluent temperature of the reaction effluent flowing in conduit 6. For the illustrated process, signal 26 is preferably set within a range of from about 932° F. (500° C.) to about 1200° F. (650° C.).

In response to signals 22 and 26, the temperature controller 24 establishes an output signal 28 responsive to the difference between signals 22 and 26. Signal 28 is scaled so as to be representative of the position of control valve 30 required to maintain the actual effluent temperature represented by signal 22 substantially equal to the desired effluent temperature represented by signal 26. Signal 28 is provided from temperature controller 24 to control valve 30, and control valve 30 is manipulated in response to signal 28.

The following example is presented to illustrate the unexpected effect on the decline of catalyst activity and conversion for a dehydrogenation reaction by maintaining a constant effluent temperature of a reaction carried out in a fixed-bed, fired-tube reactor.

EXAMPLE I

Isobutane and steam were introduced into a pilot plant tube reactor having a length of about 2 feet and a diameter of about 2 inches. The tube reactor was partially filled to about 14 inches high with a dehydrogenation catalyst which contained about 44 weight percent ZnO and 53.5 weight percent $Al_2O_3$ (both substantially combined as zinc aluminate, $ZnAl_2O_4$), 1.3 weight percent $SnO_2$ and 0.6 weight percent Pt. Liquid isobutane was introduced into the reactor at a feed rate of 3077 cc per hour (1,728 g/hr) and steam was introduced at a rate of about 2,125 g/hr. Accordingly the weight ratio of steam to isobutane was 1.23:1 and the molar ratio of steam to isobutane was 3.95:1. The liquid hourly space velocity of isobutane was 3.94 cc charge/cc catalyst/hour, which translates to a gas hourly space velocity at standard temperature and pressure conditions of about 890 cc charge/cc catalyst/hr. The average reaction pressure was about 50 psig.

Generally, the mixture of isobutane and steam was passed through the reactor for about 7 hours for each process cycle. Then the isobutane flow was discontinued, the reactor was purged with steam at a rate of about 2,125 g/hr for 5 minutes, and then air was introduced into the reactor for 25 minutes at a rate of about 10 standard cubic feet per hour (SCFH), and then for 25 minutes at about 20 SCFM while the steam flow remained at a rate of about 2,125 g/hr, so as to regenerate the hot catalyst. The flow of air was then discontinued and steam only was passed through the reactor for 5 minutes before isobutane was introduced again for a subsequent dehydrogenation period. In the inventive runs, heating of the reactors was set by a temperature controller responsive to the temperature of the reaction effluent to maintain a temperature of about 1,070° F. In the control runs, reactor heating was set by the temperature controller responsive to the average bed temperature.

The reactor effluent was cooled to an ambient temperature of about 77° F. and the uncondensed portion of the effluent was analyzed by gas chromatography. The main component of uncondensed effluent was isobutene. Test results for runs with reactor heating set to maintain a constant average temperature for the catalyst bed, and for runs to maintain a constant reactor effluent temperature are summarized in Table I below.

TABLE I

| Temperature Sensor Location | Number of runs | Process cycle time (hr./run) | Average of Conversion Decline | Average of yield decline (per/hr.) |
|---|---|---|---|---|
| Catalyst bed (control) | 10 | 6.4 | 2.5% | .24 |
| Reactor effluent (invention) | 17 | 6.4 | 1.3% | .08 |

Test results in Table I indicate that the isobutane conversion decline was reduced by about 48% and the isobutane yield decline was reduced to about 66% in the invention runs compared to the control runs. Accordingly, effective temperature control resulted in a significant increase of isobutene yield.

EXAMPLE II

Figure 2:
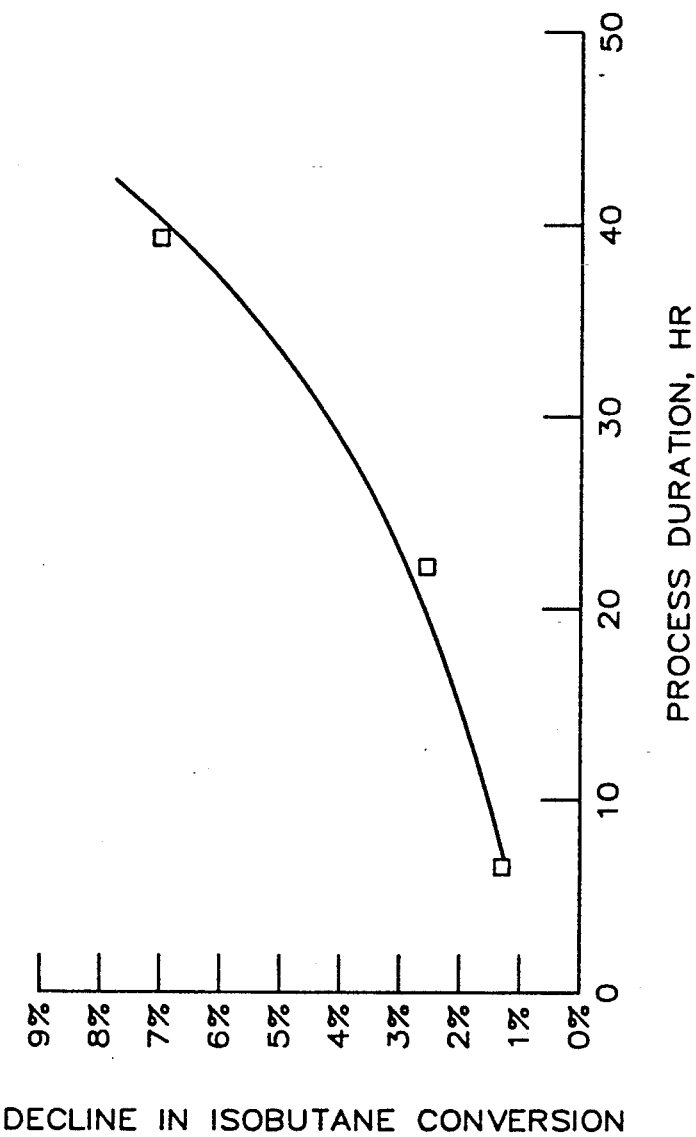
FIG. 2 graphically illustrates decline in isobutane conversion vs. process duration during operation of a pilot plant dehydrogenation reactor.

In the same manner as described for the inventive control runs in Example I, another series of runs was conducted under the same conditions and using the same catalyst but using increased process cycle times. Conversion decline data obtained in Example II, is illustrated in FIG. 2 along with the average conversion decline data for an approximately 7 hour process cycle obtained in Example I. In Example II, three runs were made for a process duration of 22.5 hours plus two additional runs made at a process duration cycle of about 40 hours to illustrate the effects extended cycle times on conversion decline using reactor effluent temperature control.

The temperature control scheme of this invention which maintains a constant temperature for reactor effluent has been found to provide a more uniform conversion of feed to products and byproducts. Accordingly, more uniform feed is provided to separation equipment downstream of the reactor vessel, which in a commercial operation results in a smoother overall process.

Specific control components used in the practice of of this invention, as illustrated in FIG. 1, such as temperature transducer 20, temperature controller 24 and control valve 30, are each well known commercially available controller components such as are described at length in *Perry's Chemical Engineering Handbook*, Sixth Edition, Chapter 22, McGraw-Hill.

While the invention has been described in terms of the presently described embodiments, reasonable variations and modifications are possible by those skilled in the art and such variations and modifications are within the scope of the described invention.

That which is claimed is:

1. In a continuous process including the step of dehydrogenating a hydrocarbon feed stream containing at least one alkane in a reactor in the presence of steam and a steam active dehydrogenation catalyst under dehydrogenation conditions, so as to at least partially convert said at least one alkane to at least one alkene, and wherein combustion fuel for heat of reaction is supplied to said reactor through a conduit containing a control valve, the improvement comprises the steps of:

establishing a first signal representative of the actual temperature of an effluent product stream of said reactor;

establishing a second signal representative of the desired temperature of said effluent product stream;

establishing a third signal responsive to the difference between said first signal and said second signal, wherein said third signal is scaled so as to be representative of the position of said control valve required to maintain the actual temperature of said effluent product stream represented by said first signal substantially equal to the desired temperature of said effluent product stream represented by said second signal; and manipulating said control valve in response to said third signal.

2. A process in accordance with claim 1 wherein the temperature of said effluent product stream is controlled at a temperature in a range of from about 950° F. to about 1150° F., and wherein said temperature range for said effluent product stream is effective for slowing the decline in activity of said steam active dehydrogenation catalyst.

3. A process in accordance with claim 1 wherein said steam active dehydrogenation catalyst comprises:
 (i) at least one aluminate spinel selected from the group consisting of Group IIA metal aluminates and Group IIB metal aluminates;
 (ii) at least one metal selected from the group consisting of nickel, ruthenium, rhodium, palladium, osmium, iridium and platinum; and
 (iii) at least one compound of a metal selected from the group consisting of germanium, tin and lead.

4. A process in accordance with claim 1 wherein said at least one alkane is selected from the group consisting of propane, n-butane, isobutane, and isopentane.

5. A process in accordance with claim 1 wherein said dehydrogenation conditions comprise a temperature in a range of about 950° F. to about 1200° F., and a pressure in a range of about 0-200 psig.

6. A process in accordance with claim 4 wherein said reactor contains a plurality of catalyst filled tubes, said process additionally comprising the following steps:

dividing said hydrocarbon feed stream so as to establish hydrocarbon flow through each tube of said plurality of catalyst filled tubes; and combining the effluent flow from said plurality of catalyst filled tubes so as to establish said effluent product stream.

* * * * *